United States Patent
Bertini et al.

(10) Patent No.: US 12,090,070 B2
(45) Date of Patent: *Sep. 17, 2024

(54) RE-LOCATION OF MAIN BODY BYPASS BRANCH ON MULTI-BRANCHED STENT GRAFT

(71) Applicant: Medtronic Vascular, Inc., Santa Rosa, CA (US)

(72) Inventors: Timothy Bertini, Santa Rosa, CA (US); Ana Zavala, Santa Rosa, CA (US); Haley King, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/471,587

(22) Filed: Sep. 10, 2021

(65) Prior Publication Data

US 2021/0401598 A1 Dec. 30, 2021

Related U.S. Application Data

(63) Continuation of application No. 16/446,403, filed on Jun. 19, 2019, now Pat. No. 11,166,832.

(60) Provisional application No. 62/686,879, filed on Jun. 19, 2018.

(51) Int. Cl.
| | | |
|---|---|---|
| A61F 2/07 | (2013.01) | |
| A61F 2/852 | (2013.01) | |
| A61F 2/86 | (2013.01) | |
| A61F 2/954 | (2013.01) | |

(Continued)

(52) U.S. Cl.
CPC ............. *A61F 2/852* (2013.01); *A61F 2/07* (2013.01); *A61F 2/86* (2013.01); *A61F 2/954* (2013.01); *A61F 2002/065* (2013.01); *A61F 2002/9155* (2013.01); *A61F 2220/0025* (2013.01)

(58) Field of Classification Search
CPC .. A61F 2/852; A61F 2/86; A61F 2/954; A61F 2002/065; A61F 2002/9155; A61F 2220/0025; A61F 2002/061; A61F 2002/067; A61F 2/07
See application file for complete search history.

(56) References Cited

U.S. PATENT DOCUMENTS

| | | | |
|---|---|---|---|
| 8,702,791 | B2 | 4/2014 | Kelly |
| 11,166,832 | B2 * | 11/2021 | Bertini ................... A61F 2/852 |
| 2005/0010277 | A1 | 1/2005 | Chuter |

(Continued)

*Primary Examiner* — Suzette J Gherbi
(74) *Attorney, Agent, or Firm* — Brooks Kushman P.C.

(57) ABSTRACT

Methods, systems, devices and apparatuses to support the walls of one or more blood vessels and perfuse blood through the one or more blood vessels. The stent device allows perfusion through one or more vessels. The stent device includes a tubular member. The tubular member has a single body that includes a main body lumen, a bypass lumen and one or more branch lumens. The tubular member is configured to be inserted into the aorta. The main body lumen is configured to expand and support a vessel wall of the aorta and the one or more branch lumens are configured to connect to one or more extension grafts that extend within one or more branch vessels. The stent device includes multiple rings of stents. The multiple rings of stents are positioned within the tubular member and are configured to be expandable to expand the tubular member to support the tubular member against the vessel walls.

20 Claims, 9 Drawing Sheets

(51) Int. Cl.
*A61F 2/06* (2013.01)
*A61F 2/915* (2013.01)

(56) References Cited

U.S. PATENT DOCUMENTS

| | | |
|---|---|---|
| 2014/0135905 A1 | 5/2014 | Hung et al. |
| 2016/0081787 A1* | 3/2016 | Parodi ..................... A61F 2/07 |
| | | 623/1.13 |
| 2016/0278910 A1* | 9/2016 | Kelly ..................... A61F 2/852 |
| 2017/0000630 A1 | 1/2017 | Shames et al. |
| 2018/0071077 A1 | 3/2018 | Argentine et al. |
| 2018/0325653 A1 | 11/2018 | Kelly |
| 2019/0274813 A1 | 9/2019 | Kelly |
| 2020/0306064 A1 | 10/2020 | Perkins et al. |
| 2020/0352699 A1 | 11/2020 | Guo et al. |
| 2020/0352700 A1 | 11/2020 | Torrance et al. |
| 2020/0352703 A1 | 11/2020 | Greenberg et al. |
| 2020/0360161 A1 | 11/2020 | Shahriari |
| 2020/0375722 A1 | 12/2020 | Ehnes |
| 2020/0405470 A1 | 12/2020 | Majercak et al. |
| 2021/0000586 A1 | 1/2021 | Perkins et al. |
| 2021/0267748 A1* | 9/2021 | Bertini ..................... A61F 2/07 |
| 2021/0353442 A1* | 11/2021 | Perkins ................... A61F 2/852 |
| 2021/0401598 A1* | 12/2021 | Bertini ................... A61F 2/852 |
| 2022/0401209 A1* | 12/2022 | Perkins ..................... A61F 2/07 |

* cited by examiner

RE-LOCATION OF MAIN BODY BYPASS BRANCH ON MULTI-BRANCHED STENT GRAFT

CROSS-REFERENCE TO RELATED APPLICATIONS

This application is a Continuation of and claims the benefit of U.S. patent application Ser. No. 16/446,403, filed Jun. 19, 2019, and issued as U.S. Pat. No. 11,166,832 on Nov. 9, 2021, which claims priority to and the benefit of U.S. Provisional Patent Application No. 62/686,879 titled "RE-LOCATION OF MAIN BODY BYPASS BRANCH ON MULTI-BRANCHED STENT GRAFT," filed on Jun. 19, 2018, and the entirety of which are hereby incorporated by reference herein.

BACKGROUND

1. Field

This specification relates to a system, a device, a method and/or an apparatus for a stent device with multiple branches or bypass lumens.

2. Description of the Related Art

Aneurysms occur in blood vessels in various locations due to age, disease, or genetic disposition, and insufficient blood vessel strength or resiliency may cause blood vessel walls to weaken and lose shape as the blood flows through the weakened blood vessels. Left untreated, these weakened blood vessels may continue to expand to the point where the blood vessel wall cannot hold, and the blood vessel may fail at the weakened locations, which may result in fatal consequences.

Many implantable medical devices are used and advantageously inserted to prevent rupture of an aneurysm. For example, a stent graft may be introduced, deployed and secured in a location with the blood vessel such that the stent graft spans the weakened areas of the blood vessel. The outer wall of the stent graft may abut and seal against the interior wall of the blood vessel to assist in channeling the blood flow to reduce any stress to the walls of the blood vessel at the weakened location.

Aneurysms may occur in a variety of locations within the aorta, some of which may not be treatable by conventional stent grafts. For example, conventional stent grafts may block branch arteries, which may result in inadequate blood flow to the associated parts of the body. Accordingly, there is a need for a system, a device, a method and/or an apparatus for a stent device with multiple branch or bypass lumens.

SUMMARY

In general, one aspect of the subject matter described in this specification is embodied in a device, a system and/or an apparatus to support the walls of one or more blood vessels. The stent device allows perfusion through one or more vessels. The stent device includes a tubular member. The tubular member has a single unitary body that includes a main body lumen, a bypass lumen and one or more branch lumens. The tubular member is configured to be inserted into the aorta. The main body lumen is configured to expand and support a vessel wall of the aorta and the one or more branch lumens are configured to connect to one or more extension grafts that expand within one or more branch vessels. The stent device includes multiple rings of stents. The multiple rings of stents are positioned within the tubular member and are configured to be expandable to expand the tubular member to support the tubular member against the vessel walls.

These and other embodiments may optionally include one or more of the following features. The one or more vessels may include the aorta, a celiac artery, superior mesenteric artery (SMA), a right renal artery and/or a left renal artery. The tubular member may be configured to allow perfusion through the one or more vessels. The main body lumen may have an inner wall and the bypass lumen may be located proximally to the inner wall of the main body lumen. The bypass lumen may be connected to the inner wall of the main body lumen to avoid obstruction of the one or more branch lumens. The bypass lumen may be connected at a position that offsets from a top of the main body lumen. The bypass lumen may terminate at or near a point of separation between the one or more branch lumens and the bypass lumen.

The stent device may have a total coverage length, from a proximal aortic seal to a celiac artery of less than 8 cm, such as 5 to 8 cm or 5 to 6 cm. The single unitary body may allow the tubular member to be arranged to minimize coverage of vessels. The tubular member may be made from a woven polyester and each ring of the multiple rings of stents may be made from nitinol. The main body lumen, the bypass lumen and/or the one or more branch lumens may be connected but do not require overlap, connectors or fasteners to connect to form the single unitary body of the tubular member. The single unitary body may reduce the amount of coverage length of the tubular member and may reduce the number of failure points in comparison to a modular tubular member.

In another aspect, the subject matter is embodied in a stent device for perfusion of one or more vessels. The stent device includes a tubular member. The tubular member has a main body lumen, a bypass lumen and one or more branch lumens. The tubular member is configured to be inserted into an aorta. The main body lumen is configured to expand and support a vessel wall of the aorta. The bypass lumen is located and positioned within the main body lumen at a position that is offset from a top of the main body lumen. The stent device includes multiple rings of stents. The multiple rings of stents are positioned within the tubular member. The multiple rings of stents are configured to expand the tubular member to support the tubular member against the vessel walls.

In another aspect, the subject matter is embodied in a stent device. The stent device has a tubular member and multiple rings of stents. The tubular member has a single unitary body including a main body lumen, a bypass lumen and one or more branch lumens. The tubular member is configured to be inserted into an aorta. The main body lumen is configured to expand and support a vessel wall of the aorta. The bypass lumen is located and positioned within the main body lumen at a position that is offset from a top of the main body lumen. The stent device includes multiple rings of stents positioned within the tubular member. The stent device is configured to be expandable to expand the tubular member to support the tubular member against the vessel walls.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views.

DETAILED DESCRIPTION

Disclosed herein are systems, devices, methods and/or apparatuses for a stent device. The stent device may be formed as a single unitary body that has a main body lumen, a bypass lumen and one or more branch lumens. The stent device may be inserted into the aorta and the one or more branch lumens may be connected to or otherwise coupled with one or more extension grafts that are inserted into one or more branch vessels such as the celiac artery, the superior mesenteric artery, the right renal artery and/or the left renal artery. As a single unitary body, the main body lumen, the bypass lumen and the one or more branch lumens are integrally formed as a single piece that is deployed in an already complete state. This may be in contrast to modular device deployments where a first device is deployed in the patient and then a secondary device is deployed in the patient that couples or connects to the first device (e.g., like the extension grafts discussed, below). The terms unitary body and integrally formed may include that the various portions are permanently connected together, such as by stitching. This reduces the amount of coverage length of the stent device and the number of failure points in comparison to a stent device that is modular.

Other benefits and advantages include re-locating the bypass lumen inside into the main body lumen. By having the bypass lumen located within the main body lumen, instead of extending outward away from the main body lumen, the bypass lumen does not obstruct the one or more branch lumens. This allows for a better and easier view of the different lumens within the stent device when viewed under fluoroscopy because there are less lumens that may overlap one another. Moreover, this allows for an extension graft to be connected to the bypass lumen without obstructing the one or more branch lumens. Additionally, the bypass lumen may be positioned within the main body lumen and offset from the top of the main body lumen. This allows for another stent graft to be connected to or coupled with the top of the main body lumen, for example.

Figure 1A:
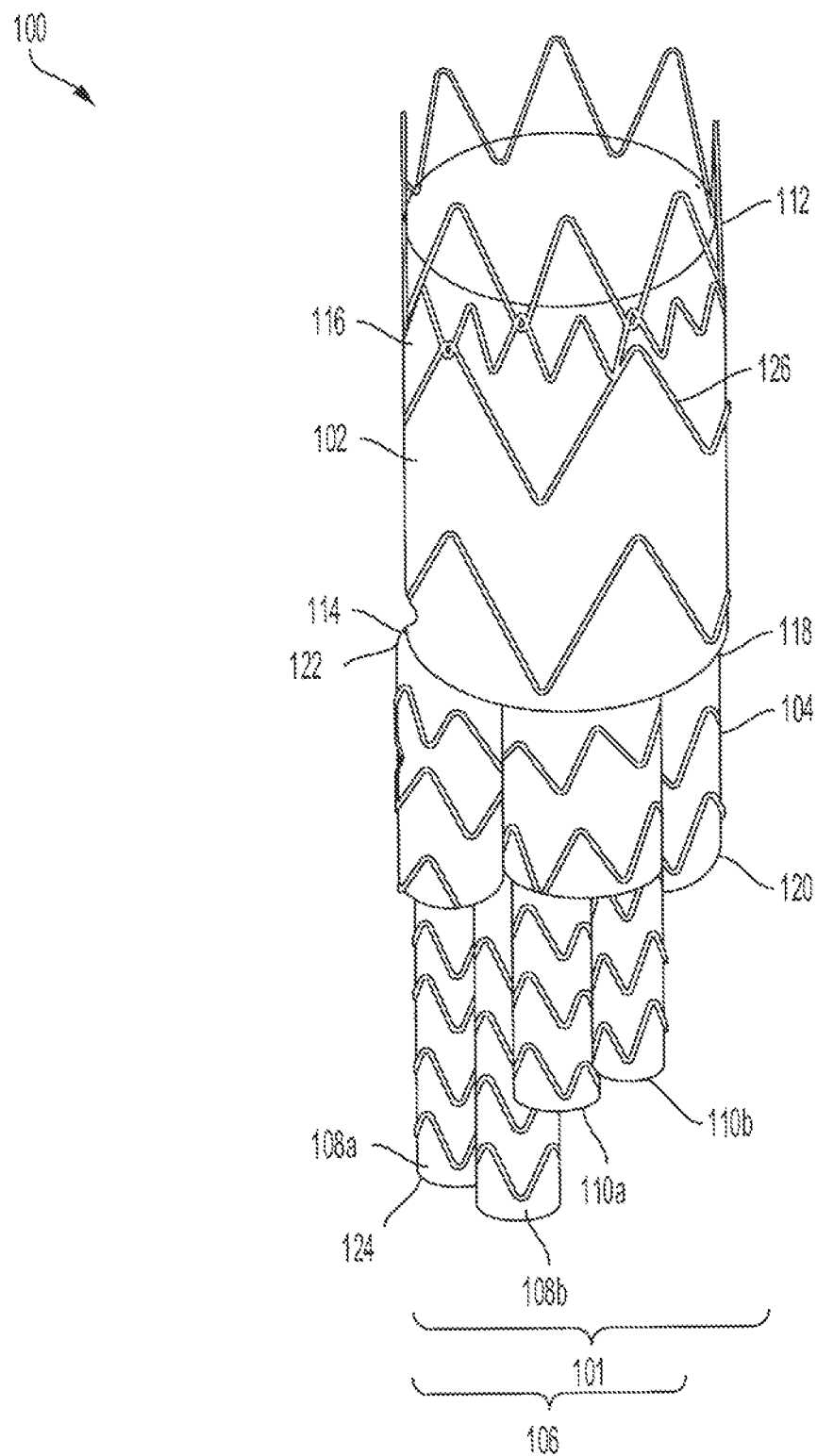
FIG. 1A shows an example unibody stent graft according to an aspect of the invention.
Figure 1B:
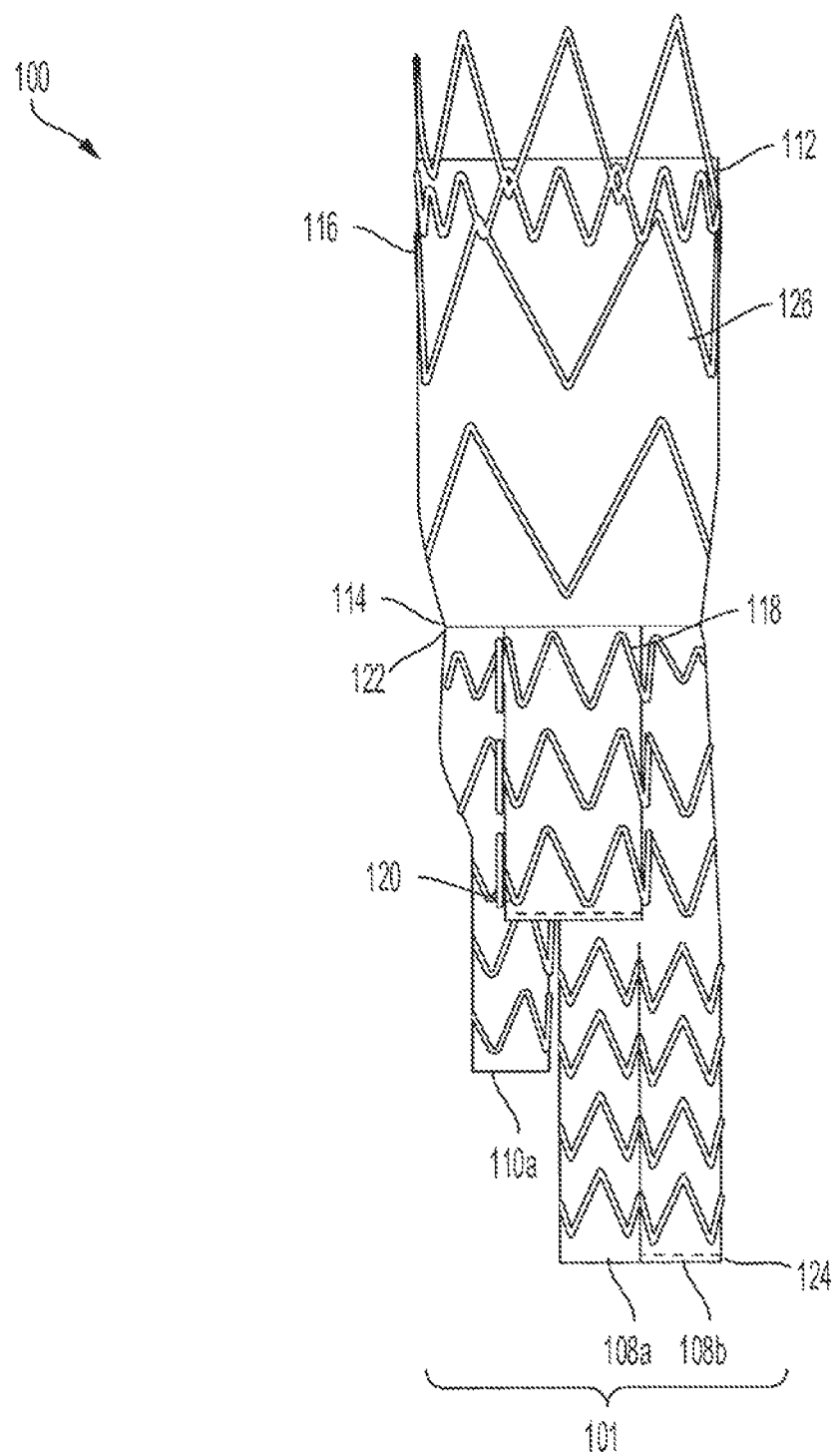
FIG. 1B shows an example side-perspective view of the unibody stent graft of FIG. 1A according to an aspect of the invention.

FIG. 1 shows a stent graft 100. The stent graft 100 may have a tubular member 101 and multiple rings of stents 126. The tubular member 101 includes a main body lumen 102, a bypass lumen 104 and one or more branch lumens 106. The multiple rings of stents 126 may be positioned on the outside of the tubular member 101, on the inside of the tubular member 101, or within the tubular member 101, such as in between layers, and may be self-expanding or balloon expanding. The stents 126 may be attached to the tubular member by stitching. The multiple rings of stents 126 support the tubular member 101 against the vessel walls of the one or more blood vessels. When the stent graft 100 is deployed, each ring of stents 126 of the multiple rings of stents 126 may expand along a circumference of the stent graft 100 to position the tubular member 101 against the vessel walls of the one or more blood vessels to provide support to the vessel walls and allow blood to perfuse through the one or more blood vessels.

The stent graft 100 allows blood to perfuse through one or more blood vessels and supports the wall of the one or more blood vessels. The stent graft 100 may be substantially cylindrical to maintain a complete seal with the wall of the one or more blood vessels. A stent graft 100 refers to a prosthesis that includes a stent and a graft material that forms one or more lumens within a blood vessel, such as the tubular member 101. The stent may be a made of any suitable material, such as a nitinol, stainless steel, nickel and/or titanium, and/or a bio compatible plastic. The stent may be composed of multiple rings and may be of any shape, such as a sinusoidal, zig-zag or v-shaped ring. The graft may be made from a graft material, such as a biocompatible fabric, a woven polyester, fluorinated polymer include polytetrafluoroethylene (PTFE) and expanded polytetrafluoroethylene (ePTFE) or other biocompatible fabric. The graft may be shaped into the tubular member 101.

The tubular member 101 may be a single unitary body formed from various portions that when shaped by the stents form the different lumens. The various portions are in fluid communication with each other and formed together to form the single unitary body. Since the graft has a unitary body, there are less failure points where the different portions of the graft may become disjointed, disconnected or otherwise fail to support a weakened portion of one or more blood vessels in comparison to a modular stent graft that has a modular tubular member with multiple portions fastened or otherwise connected together in the patient. The stent may be sandwiched in between the layers of the graft and/or may be interwoven with the graft to form the stent graft 100 and shaped to form the tubular member 101 with the different lumens.

Figure 5:
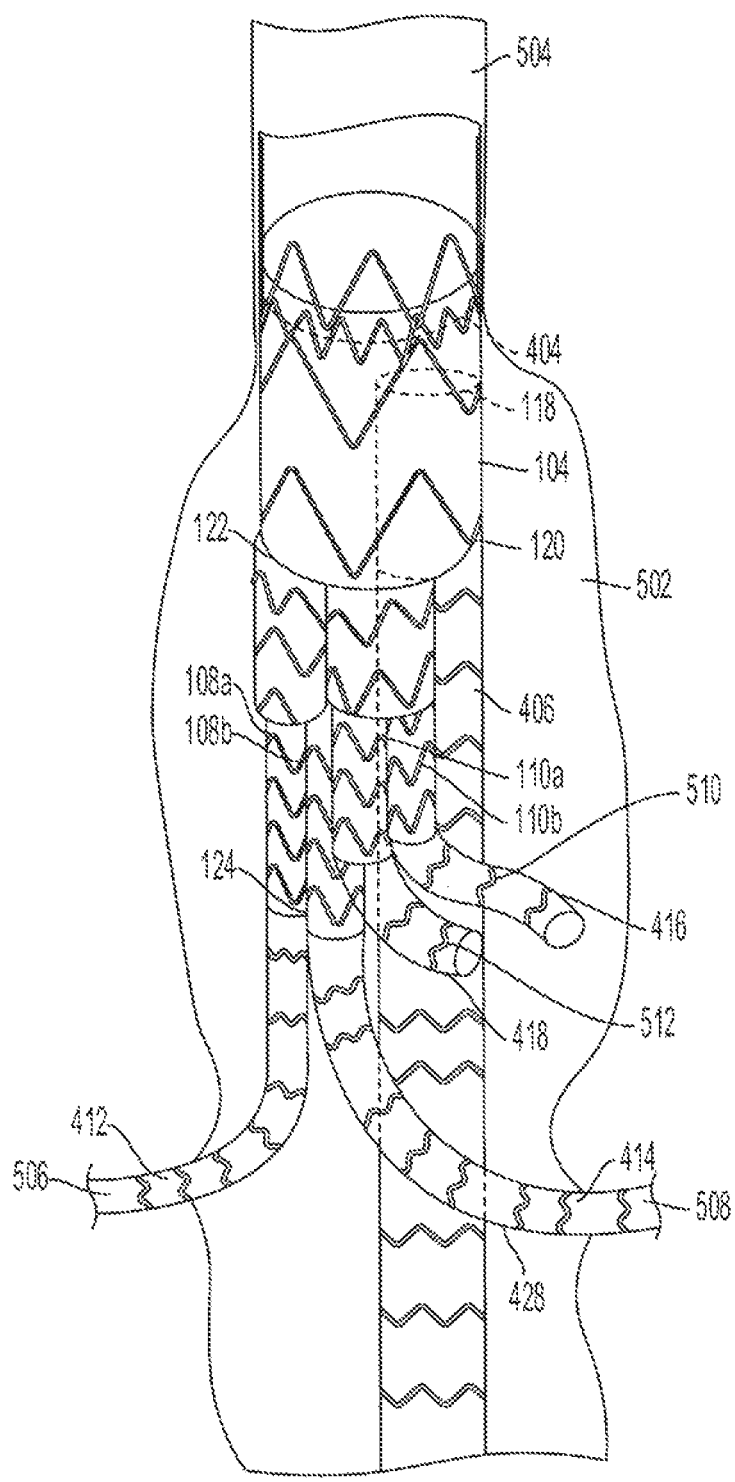
FIG. 5 shows a cross-sectional view of the unibody stent graft of FIG. 1 positioned within the aorta to address aortic aneurysms and allow perfusion of blood according to an aspect of the invention.

The main body lumen 102 has a proximal end 112 and a distal end 114. The proximal end refers to a portion that is positioned closest to the heart, and the distal end refers to a portion that positioned away from and farthest from the heart. The main body lumen 102 may extend a longitudinal length of approximately 40-80 mm and may be positioned within the descending aorta 504, which is distal of the aortic arch, to support the inner surface of the vessel walls of the descending aorta, as shown in FIG. 5 for example. In one embodiment, the main body lumen 102 may have a length of 45 to 75 mm, 50 to 70 mm, or 55 to 65 mm. The total coverage length, from a proximal aortic seal to the celiac artery 510, may be less than 8 cm, such as 5 to 8 cm or 5 to 6 cm, and may be arranged to minimize coverage of other vessels.

The main body lumen 102 defines a tubular wall 116 that may be continuous with the bypass lumen 104, and the one or more branch lumens 106 such that any fluid entering the main body lumen 102 must exit through one of the bypass lumen 104 or the one or more branch lumens 106. That is, the main body lumen 102 is in fluid communication with the bypass lumen 104 and the one or more branch lumens 106.

The bypass lumen 104 and the one or more branch lumens 106 are in fluid communication with the main body lumen 102. The bypass lumen 104 and the one or more branch lumens 106 may each have a proximal end 118, 122, respectively, that is connected to, coupled to or integrally formed with the distal end 114 of the main body lumen 102. In some implementations, the proximal end 118 of the bypass lumen 104 is connected to, coupled to or integrally formed near the proximal end 112 of the main body lumen 102. The bypass lumen 104 and the one or more branch lumens 106 may have a distal end 120, 124, respectively, that are opposite the proximal ends 118, 122, respectively. The distal ends 120, 124 have an opening that allows the fluid or the blood to perfuse or exit into the one or more blood vessels.

Figure 4:
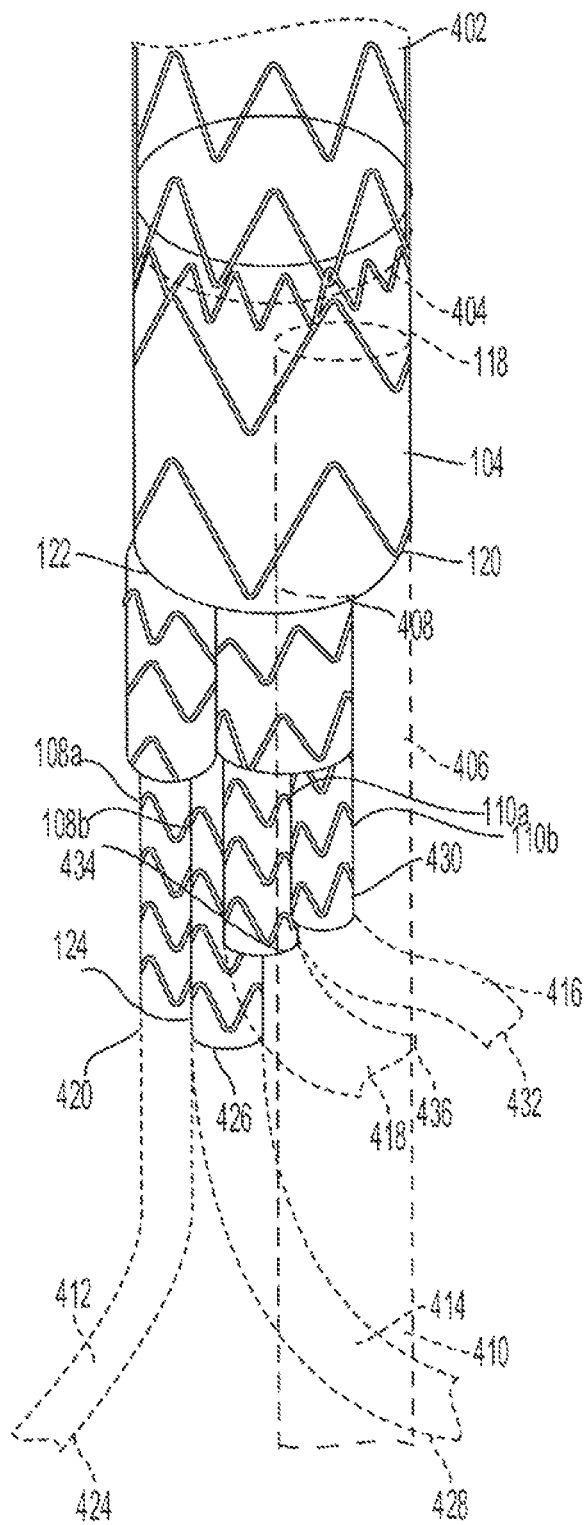
FIG. 4 shows an example view of multiple extension grafts connecting and/or interfacing with the unibody stent graft of FIG. 1 that has the re-located bypass lumen according to an aspect of the invention.

When the main body lumen 102 is positioned within the descending aorta, the one or more branch lumens 106 may be connected to one or more extension grafts that are positioned within one or more branch vessels when deployed. FIG. 4 further describes the one or more extension grafts. The one or more branch lumens 106 may be in fluid communication with the main body lumen 102 and the bypass lumen 104. The one or more branch lumens 106 may include any number of and/or any number of sets of branch lumens to branch into and perfuse blood through the one or more extension grafts within the one or more branch vessels. The one or more branch lumens 106 may include multiple branch lumens 106 including a first set of branch lumens 108*a-b* and a second set of branch lumens 110*a-b*. The first set of branch lumens 108*a-b* may be longer in length than the second set of branch lumens 110*a-b* and may extend farther distally from the main body lumen 102 than the second set of branch lumens 110*a-b*.

When the main body lumen 102 is expanded and/or is deployed, the main body lumen 102 may support the vessel walls of the descending aorta 504, the first set of branch lumens 108*a-b* may be connected to one or more extension grafts that may be positioned within and support the vessel walls of the one or more renal arteries 506, 508. The first set of branch lumens 108*a-b* may be positioned near or in proximity to the one or more renal arteries 506, 508. The second set of branch lumens 110*a-b* may be connected to one or more other extension grafts that may be positioned within and support the vessel walls of the celiac artery 510 and/or the SMA 512. The second set of branch lumens 110*a-b* may be positioned near or in proximity to the celiac artery 510 and/or the SMA 512. This allows perfusion of blood through the descending aorta 504, the one or more renal arteries 506, 508, the celiac artery 510 and/or the SMA 512.

Figure 2A:
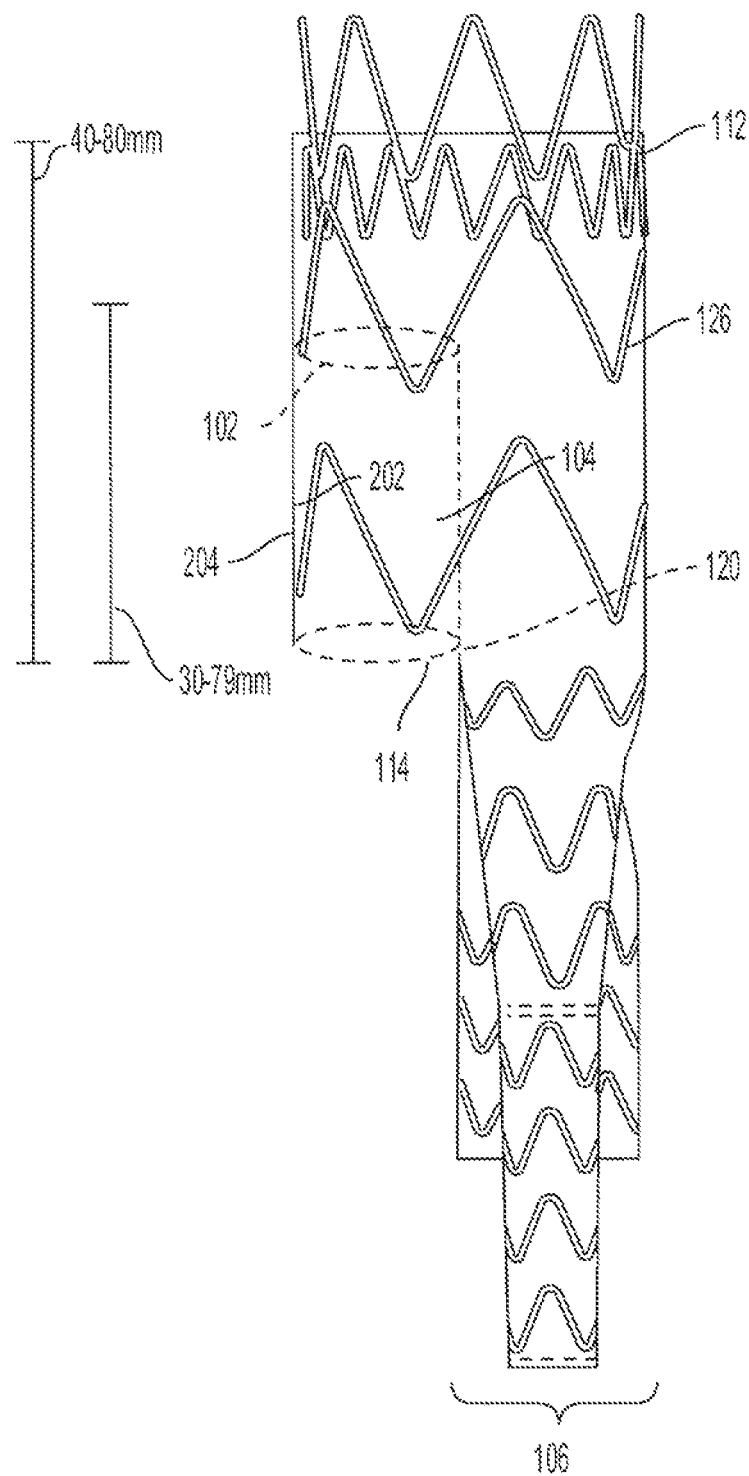
FIG. 2A shows an example of the unibody stent graft of FIG. 1 that has the bypass lumen re-located within and integrally formed with the main body lumen according to an aspect of the invention.
Figure 2B:
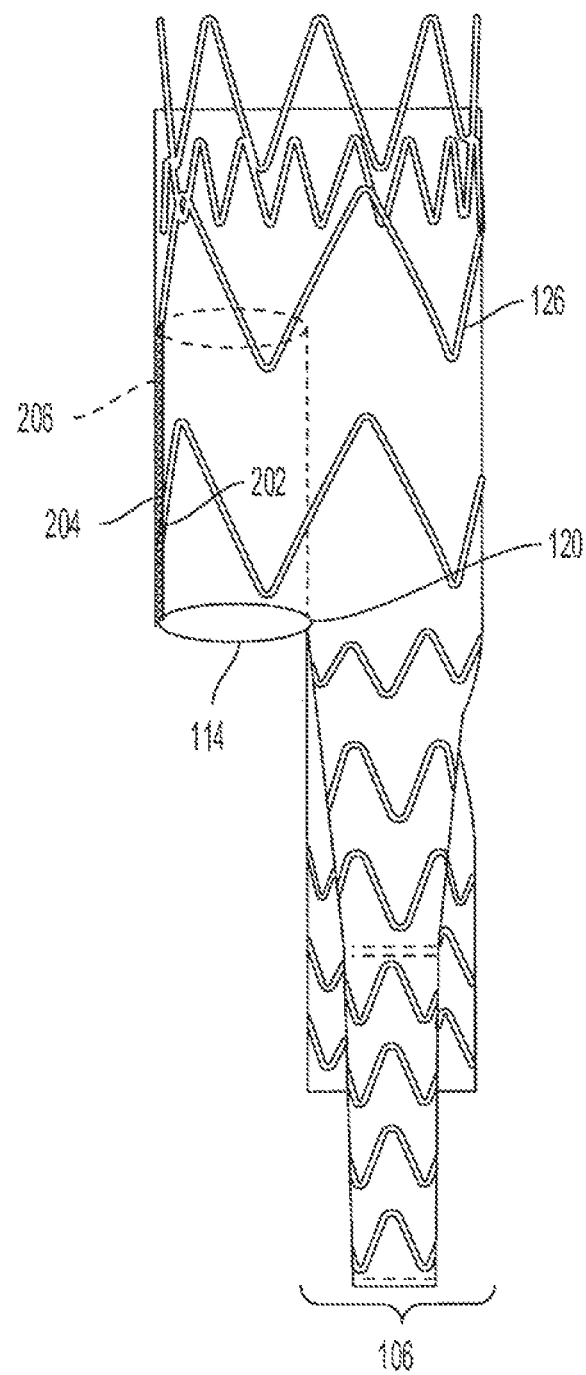
FIG. 2B shows an example of the unibody stent graft of FIG. 1 that has the bypass lumen re-located within and fastened to the main body lumen according to an aspect of the invention.

The bypass lumen 104 may have a longitudinal length greater than 30 mm, but when the bypass lumen 104 is positioned within the main body lumen 102 and offset from an opening in the main body lumen 102, the bypass lumen 104 may have a longitudinal length of approximately 30-79 mm. The bypass lumen 104 may have a proximal end 118 that is positioned near or in proximity to the proximal end 112 of the main body lumen 102 but offset a distance from the opening at the proximal end 112 of the main body lumen 102, as shown in FIGS. 2A-2B for example. In one embodiment, the length of the bypass lumen 104 may be shorter than the main body lumen 102 by 10 mm or less, of which some example lengths are disclosed above. Accordingly, if the main body lumen has a length of 45 to 75 mm, then the bypass lumen may be at least 35 mm and less than 75 mm. In other embodiments, the bypass lumen 104 may be shorter by 5 mm or less.

FIGS. 2A-2B show the bypass lumen 104 re-located within the main body lumen 102. Here, the bypass lumen 104 is positioned entirely within the main body lumen 102 but is offset a distance, such as a distance of approximately 1-3 mm distally or below an opening on the proximal end 112 of the main body lumen 102. The bypass lumen 104 may extend distally within the main body lumen 102 to the distal end 114 of the main body lumen 102 and the proximal ends 122 of the one or more branch lumens 106, such that no shoulder or branch is formed at the juncture of the distal end 120 of the bypass lumen 104 and an adjacent branch lumen of the one or more branch lumens 106. That is, the bypass lumen 104 may not extend outward from within the main body lumen 102 and ends or terminates at or near a point of separation between the one or more branch lumens 106 and the bypass lumen 104. In some implementations, the bypass lumen 104 may not be offset from the opening of the main body lumen 102.

The bypass lumen 104 may be connected to, coupled with or integrally formed with an inner wall 202 of the main body lumen 102. That is, an outer wall 204 of the bypass lumen 104 and the inner wall 202 of the main body lumen 102 may share the same boundary and/or be the same wall. The shared boundary and/or the shared portion of the walls 202, 204 may run in a longitudinal direction from the proximal end 118 of the bypass lumen 104 to the distal end 120 of the bypass lumen 104. The outer wall 204 may be fastened, coupled, or otherwise connected to the inner wall 202 using a fastener 206, such as a stitching, as shown in FIG. 2B for example. The fastener 206 may be positioned to connect a portion of the inner wall 202 and the outer wall 204 or may run along the entire length of the shared boundary between the inner wall 202 and the outer wall 204. The fastener 206 may be a single stitch that runs along a shared portion of the walls 202, 204, as shown in FIG. 3D for example, or may be multiple stitches that run along the shared portion of the walls 202, 204, as shown in FIG. 3E for example. In some implementations, the outer wall 204 of the bypass lumen 104 and the inner wall 202 of the main body lumen 102 may be coupled without use of a fastener, connector or other fastening means. For example, the outer wall 204 and the inner wall 202 may be the same wall and/or integrally formed, as shown in FIG. 2A.

Figure 3A:
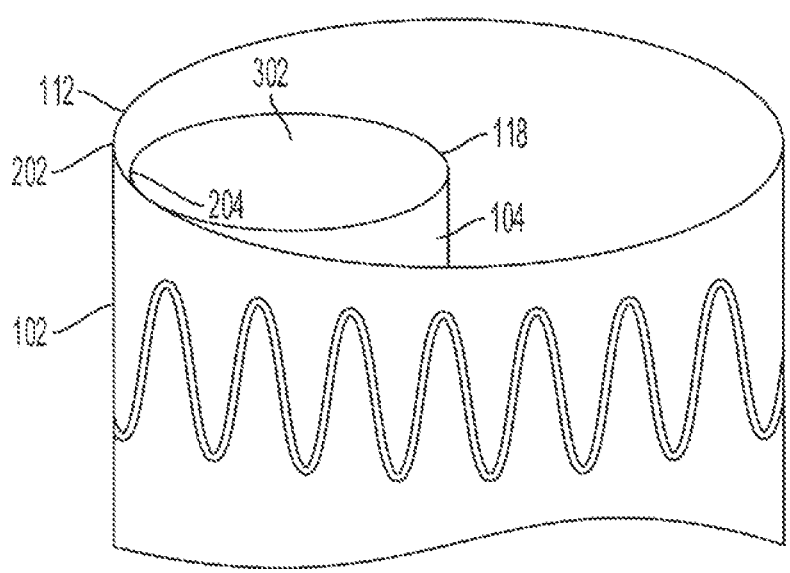
FIG. 3A shows an example interior view of the bypass lumen disposed within the main body lumen of the unibody stent graft of FIG. 1 according to an aspect of the invention.
Figure 3B:
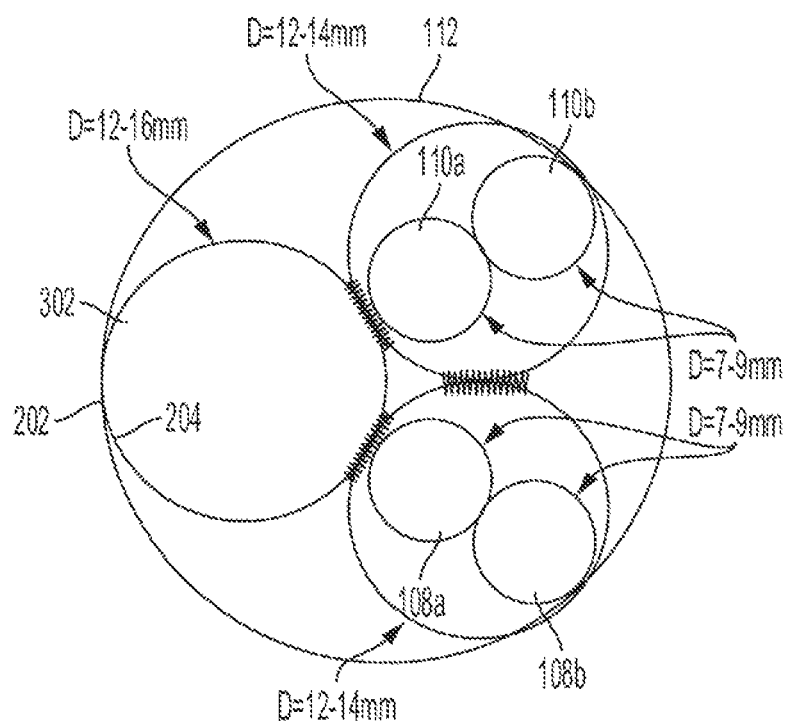
FIG. 3B shows a top-down perspective view of the unibody stent graft of FIG. 1 according to an aspect of the invention.
Figure 3C:
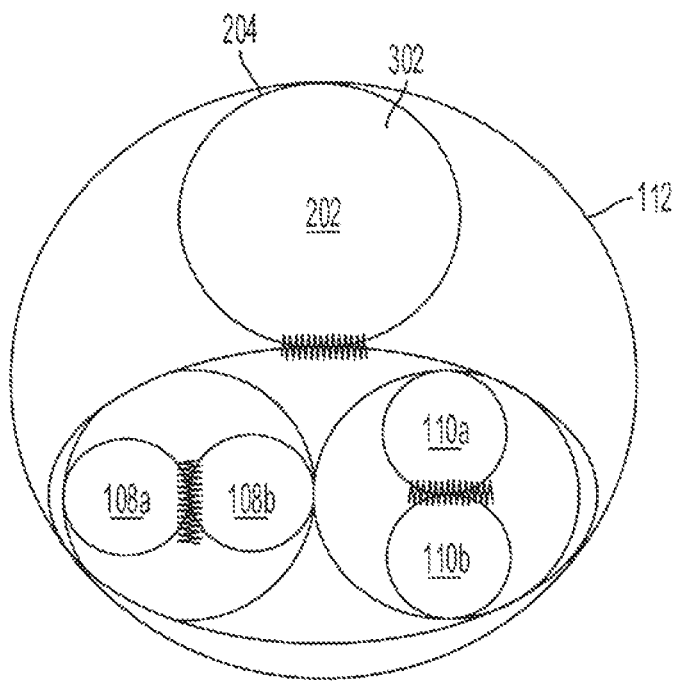
FIG. 3C shows another top-down perspective view of the unibody stent graft of FIG. 1 according to an aspect of the invention.
Figure 3D:
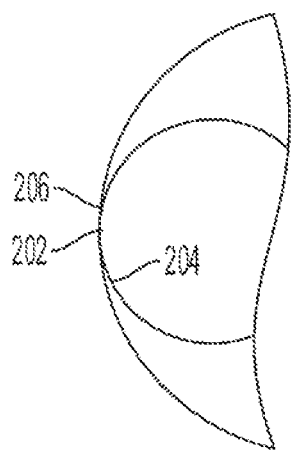
FIG. 3D shows an example interface between the bypass lumen and the main body lumen of the unibody stent graft of FIG. 1 that uses a single stitch along the entire interface according to an aspect of the invention.
Figure 3E:
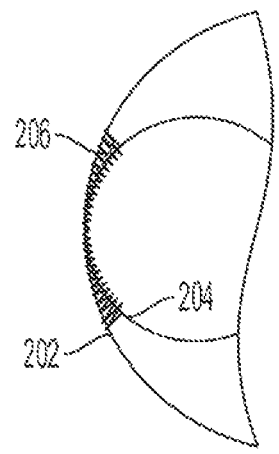
FIG. 3E shows another example interface between the bypass lumen and the main body lumen of the unibody stent graft of FIG. 1 that uses multiple stitches along the entire interface according to an aspect of the invention.

FIGS. 3A-3C also show the bypass lumen 104 disposed within the main body lumen 102. When the stent graft 100 is deployed, the bypass lumen 104 is a single internal channel 302 within the main body lumen 102 that extends distally or downward within the main body lumen 102 and that has an outer wall 204 that is attached, connected, coupled, integrally formed or otherwise interfaces or is shared with an inner wall 202 of the main body lumen 102. FIG. 3A shows the bypass lumen 104 offset slightly from the opening near the proximal end 112 of the main body lumen 102 to form the single internal channel 302. FIGS. 3B-3C show top-down perspective views of the single internal channel 302 and the first set of branch lumens 108*a-b* and the second set of branch lumens 110*a-b*. The diameter of the single internal channel 302 may be approximately 12-16 mm. Moreover, each set of branch lumens 108*a-b*, 110*a-b* of the one or more branch lumens 106 may have an opening of approximately 12-14 mm and each opening of the one or more branch lumens 106 may be approximately 7-9 mm.

Since the bypass lumen 104 is positioned or re-located within the main body lumen 102 and does not extend outward distally from the main body lumen 102, the bypass lumen 104 does not interfere with or obstruct the one or more branch lumens 106. Moreover, when the stent graft 100 is deployed, since the bypass lumen 104 is re-located within the main body lumen 102, the bypass lumen 104 does not obstruct the view of the one or more branch lumens 106 and/or other lumens while viewed under fluoroscopy.

When the bypass lumen 104 is offset the distance from the opening of the main body lumen 102, a first extension graft 402 may be connected to the proximal end 112 of the main body lumen 102. When the bypass lumen 104 is positioned within the main body lumen 102 and the bypass lumen 104 does not extend outward from the main body lumen 102, the bypass lumen 104 does not obstruct or otherwise interfere with the one or more branch lumens 106, which allows a second extension graft 406 to be connected to the distal end 120 of the main body lumen 102.

FIG. 4 shows different extension grafts 402, 406 that may be connected to the main body lumen 102 when the bypass lumen 104 is located entirely within the main body lumen 102 and positioned with an offset from the opening of the main body lumen 102. The first extension graft 402 may have a proximal end (not shown) and a distal end 404 that connects to or inserts into the proximal end 112 of the main body lumen 102. The first extension graft 402 may be positioned above the stent graft 100, e.g., in an upper portion of the descending aorta, and extend distally within the descending aorta and be connected to the proximal end 112 of the main body lumen 102, as shown in FIG. 4 for example. Moreover, when the bypass lumen 104 is within the main body lumen 102 and does not extend outward from the main body lumen 102, a second extension graft 406 may connect to the bypass lumen 104 and/or the main body lumen 102. The second extension graft 406 may have a proximal end 408 and a distal end 410. The proximal end 408 of the second extension graft 406 may connect to and/or be inserted into the distal end 120 of the bypass lumen 104 and/or the distal end 114 of the main body lumen 102.

The second extension graft 406 may be adjacent to the one or more branch lumens 106 and extend farther distally down the descending aorta than the one or more branch lumens 106 when deployed. The second extension graft 406 may be connected to the bypass lumen 104 after the other extension grafts have been deployed (e.g., to the renal, celiac, and SMA arteries). The distal end 410 of the second extension graft 406 may be anchored or sealed in the aorta between the renal arteries and the iliac bifurcation, if there is a suitable non-aneurysmal landing zone. If there is no suitable landing zone, bifurcated modular component may be connected/inserted into the distal end 410 of the second extension graft 406. This provides for a mechanism to gain seal in both iliac arteries.

Other extension grafts 412, 414, 416, 418 may connect to one or more branch lumens 106. A third extension graft 412 and a fourth extension graft 414 may each be connected to one branch lumen of the first set of branch lumens 108*a-b*. The third extension graft 412 and the fourth extension graft 414 each have a proximal end 420, 426, respectively, and a distal end 424, 428, respectively. The proximal ends 420, 426 may connect to and/or be inserted into the distal ends 124 of the first set of branch lumens 108*a-b* and may be positioned within the one or more renal arteries 506, 508. A fifth extension graft 416 and a sixth extension graft 418 may each be connected to one branch lumen of the second set of branch lumens 110*a-b*. The fifth extension graft 416 and the sixth extension graft 418 each have a proximal end 430, 434, respectively, and a distal end 432, 436, respectively. The proximal ends 430, 434 may connect to and/or be inserted into the distal ends 124 of the second set of branch lumens 110*a-b* and may be positioned within the celiac artery 510 or SMA 512.

While the extension grafts 412, 414, 416, and 418 are referred to herein in the singular context, it is to be understood that two or more extension grafts may be linked together to form an overall extension graft assembly. For example, since the distance to the renal arteries may be longer than to the celiac or SMA arteries, two or more extension grafts may be linked together such that a first extension graft is coupled to the distal ends 124 of the branch lumens 108*a/b* and a final (second, third, fourth, etc.) extension graft is coupled to the first extension graft (possibly through intermediate grafts) and extends into a renal artery. Similar extension graft assemblies may be used for the celiac and/or SMA arteries.

FIG. 5 shows a cross-sectional view of the stent graft 100 positioned within the descending aorta 504 to address an aortic aneurysm 502 and allow perfusion of blood. The main body lumen 102 may be positioned within the descending aorta 504, which is distal of the aortic arch, to support the inner surface of the vessel walls of the descending aorta 504. The one or more branch lumens 106 may be configured to receive extensions grafts that then extend within one or more branch vessels including the one or more renal arteries 506, 508, the celiac artery 510 and/or the superior mesenteric artery (SMA) 512. The first set of branch lumens 108*a-b* may be longer in length than the second set of branch lumens 110*a-b* in order to connect extension grafts that may be deployed into one or more branch vessels that are farther distally from the aortic arch. For example, since the one or more renal arteries 506, 508 are farther distally from the aortic arch, the longer of the first set of branch lumens 108*a-b* and the second set of branch lumens 110*a-b*, i.e., the first set of branch lumens 108*a-b*, may be positioned closer to the one or more renal arteries 506, 508. Whereas, the other set of branch lumens, i.e., the second set of branch lumens 110*a-b*, which are shorter in length than the first set of branch lumens 108*a-b*, may be positioned closer to the celiac artery 510 and/or SMA 512, which are more proximal to the aortic arch than the one or more renal arteries 506, 508. However, the relative lengths described above are not intended to be limiting. In other embodiments, the lumens may all have the same or similar length, or the relative lengths may be reversed (e.g., renal lumens are shorter than celiac/SMA lumens).

Exemplary embodiments of the methods/systems have been disclosed in an illustrative style. Accordingly, the terminology employed throughout should be read in a non-limiting manner.

What is claimed is:

1. A stent device for perfusion of one or more vessels, comprising:
    a tubular member having a single unitary body including a main body lumen, a bypass lumen and one or more branch lumens, the tubular member configured to be inserted into an aorta, the main body lumen being configured to expand and contact a vessel wall of the aorta, the bypass lumen being located completely within the main body lumen and each one or more branch lumens configured to couple to one or more extension grafts to allow blood to perfuse through one or more branch vessels; and
    a plurality of stent rings secured to the tubular member and configured to be expandable to expand the tubular member to contact the vessel walls;
    wherein:
        the main body lumen has a proximal end and a distal end,
        the bypass lumen has a proximal end and a distal end,
        the one or more branch lumens have a proximal end and a distal end, and
        the distal end of the bypass lumen is aligned with the distal end of the main body lumen and the proximal end of the one or more branch lumens.

2. The stent device of claim 1, wherein the main body lumen has an inner wall and the bypass lumen has an outer wall, wherein the bypass lumen is positioned within the main body lumen to form a single channel within the main body lumen, wherein the inner wall of the main body and the outer wall of the bypass lumen interface, connect or are integrally formed and the bypass lumen does not extend beyond or outward from the main body lumen.

3. The stent device of claim 2, wherein the bypass lumen is connected to the inner wall of the main body lumen to avoid obstruction of the one or more branch lumens, wherein the bypass lumen is connected at a position that offsets from a top of the main body lumen.

4. The stent device of claim 3, wherein an end of the bypass lumen terminates at or near a point of separation between the one or more branch lumens and the bypass lumen.

5. The stent device of claim 1, wherein a total coverage length, from a proximal aortic seal to a celiac artery, is less than 8 cm and the single unitary body allows the tubular member to be arranged to minimize coverage of vessels.

6. The stent device of claim 1, wherein the main body lumen, the bypass lumen and the one or more branch lumens are permanently connected to form the single unitary body of the tubular member, which reduces an amount of coverage length of the tubular member and a number of failure points in comparison to a modular tubular member.

7. The stent device of claim 1, wherein the tubular member is made from a woven polyester and each of the plurality of stent rings is made from nitinol.

8. A stent device for perfusion of one or more vessels, comprising:
    a tubular member having a main body lumen, a bypass lumen and one or more branch lumens, the tubular member configured to be inserted into an aorta, the main body lumen being configured to expand and contact a vessel wall of the aorta and the bypass lumen being located and positioned within the main body lumen at a position that is offset from a top of the main body lumen; and
    a plurality of stent rings secured to the tubular member and configured to expand the tubular member to contact the vessel walls;
    wherein:
        the bypass lumen has a proximal end and a distal end,
        the one or more branch lumens have a proximal end and a distal end, and
        the distal end of the bypass lumen is aligned with the proximal end of the one or more branch lumens such that no shoulder or branch is formed at a juncture of the distal end of the bypass lumen and an adjacent branch lumen of the one or more branch lumens.

9. The stent device of claim 8, wherein the one or more vessels include the aorta, a celiac artery, superior mesenteric artery (SMA), a right renal artery and a left renal artery, wherein the tubular member is configured to allow perfusion through the one or more vessels.

10. The stent device of claim 8, wherein the main body lumen has an inner wall and the bypass lumen is located proximally to an inner wall of the main body lumen, and further comprising an extension graft connected to the proximal end of the main body lumen.

11. The stent device of claim 8, wherein the main body lumen, the bypass lumen and the one or more branch lumens form a single unitary body.

12. The stent device of claim 11, wherein a total coverage length, from a proximal aortic seal to a celiac artery, is less than 8 cm.

13. The stent device of claim 8, wherein the bypass lumen is connected to the inner wall of the main body lumen to avoid obstruction with the one or more branch lumens.

14. The stent device of claim 8, wherein an end of the bypass lumen terminates at or near a point of separation between the one or more branch lumens and the bypass lumen.

15. The stent device of claim 8, wherein the tubular member is made from a woven polyester and each of the plurality of stent rings is made from nitinol.

16. A stent device, comprising:
    a tubular member having a single unitary body including a main body lumen, a bypass lumen and one or more branch lumens, the tubular member configured to be inserted into an aorta, the main body lumen being configured to expand and contact a vessel wall of the aorta and the bypass lumen being located and positioned within the main body lumen at a position that is offset from a top of the main body lumen; and
    a plurality of stent rings secured to the tubular member and configured to be expandable to expand the tubular member to contact the vessel walls;
    wherein:
        the main body lumen has a proximal end and a distal end,
        the bypass lumen has a proximal end and a distal end, and
        the distal end of the bypass lumen is aligned with the distal end of the main body lumen.

17. The stent device of claim 16, wherein the tubular member is configured to allow perfusion through one or more vessels including the aorta, a celiac artery, superior mesenteric artery (SMA), a right renal artery and a left renal artery.

18. The stent device of claim 16, wherein the main body lumen has an inner wall and the bypass lumen is located proximally to an inner wall of the main body lumen, wherein the entire bypass lumen is located within the main body lumen.

19. The stent device of claim 16, wherein:
   the one or more branch lumens have a proximal end and a distal end, and
   the distal end of the bypass lumen is aligned with the proximal end of the one or more branch lumens.

20. The stent device of claim 8, wherein the main body lumen has a proximal end and a distal end, and the proximal end of the bypass lumen is aligned with the proximal end of the main body lumen.

* * * * *